United States Patent [19]

Haffer et al.

[11] Patent Number: 5,401,854
[45] Date of Patent: Mar. 28, 1995

[54] PROCESS FOR THE PRODUCTION OF INDOLE DERIVATIVES

[75] Inventors: Gregor Haffer; Helmut Börner; Wolfgang Kübler; Klaus Nickisch, all of Berlin, Germany

[73] Assignee: Schering Aktiengesellschaft, Berlin and Bergkamen, Germany

[21] Appl. No.: 987,263

[22] PCT Filed: Jul. 1, 1992

[86] PCT No.: PCT/DE92/00551

§ 371 Date: Mar. 8, 1993

§ 102(e) Date: Mar. 8, 1993

[87] PCT Pub. No.: WO93/01168

PCT Pub. Date: Jan. 21, 1993

[30] Foreign Application Priority Data

Jul. 6, 1991 [DE] Germany .................. 41 22 722.0

[51] Int. Cl.⁶ .............................................. C07D 209/08
[52] U.S. Cl. ................................... 548/469; 548/504; 548/507
[58] Field of Search ................... 548/504, 507, 469

[56] References Cited

U.S. PATENT DOCUMENTS

| 4,428,962 | 1/1984 | Bristol et al. | 548/469 |
| 4,435,403 | 3/1984 | Braestrup et al. | 424/256 |
| 4,596,808 | 6/1986 | Braestrup et al. | 514/292 |

FOREIGN PATENT DOCUMENTS

| 4013907 | 10/1991 | Germany | 514/292 |
| 1079091 | 8/1967 | United Kingdom | 514/292 |

OTHER PUBLICATIONS

CA 110(1):8073M Indole . . . (Aminomethyl) indoles. Borisova et al., p. 621, 1977.
CA 87(3):22951j An . . . system. Klohr et al., p. 742, 1989, CA 95(5):42809n Bisindoles. 8. . . . oxide. Samsoniya et al., p. 731, 1981.
CA 116(7):59098e Preparation . . . derivatives. Kuebler et al., p. 834, 1992.
CA 117(9):90139p Preparation . . . antagonists. Nakanishi, p. 767, 1992.
Chemical Abstracts, vol. 87, No. 3 (Jul. 18, 1977), Abstract No. 22951J, "Indole derivatives", p. 621.
Chemical Abstracts, vol. 75, No. 9 (Aug. 30, 1971) Abstract No. 63605V, "Indole derivatives and their intermediates", p. 437.
Chemical Abstracts, vol. 86, No. 5 (Jan. 31, 1977), Abstract No. 29624T, "Intermediates for indoles", p. 350.

*Primary Examiner*—Mary C. Lee
*Assistant Examiner*—J. K. McKane
*Attorney, Agent, or Firm*—Millen, White, Zelano & Branigan

[57] ABSTRACT

A process for the production of indole derivatives, which is characterized in that in the presence of phosphoric acid a substitution with an imine is performed, and intermediate products of this process and the production of these intermediate products are described.

13 Claims, No Drawings

PROCESS FOR THE PRODUCTION OF INDOLE DERIVATIVES

SUMMARY OF THE INVENTION

The invention relates to a process for the production of indole derivatives, new intermediate products for the production of indole derivatives as well as the process for the production of new intermediate products.

Indoles are intermediate products for the synthesis of pharmacologically suitable compounds such as, for example, for the production of tryptamines (C.A. 56, 11701 (1962), tryptophanes (R. V. Heinzelmann et al. Org. Chemie 25, 1548 (1960) and carbolines (EP-A-239667, EP-A-234 173).

Because of their good binding affinity to the benzodiazepine receptors, β-carbolines show effects on the central nervous system and therefore have just recently met with great interest in pharmaceutical research.

However it has turned out that the reaction of the indole with aldehydes and more space demanding primary amines, such as tert. butyl or isopropyl amine in glacial acetic acid is achieved in poor yields and is achieved in better yields when using the corresponding aldimines, and that the yields are greatly influenced by the substituent on the indole.

For example, the imine from methoxyacetaldehyde and isopropylamine reacts with 4- or 5-benzyloxy indole only in a yield of 60 or 64% to the target compound (EP 54 507). If, however, phenoxy indoles substituted with halogen are reacted with imines in glacial acetic acid, then the desired gramine derivatives are not obtained, but, instead besides the initial compound, a dimeric product is isolated [G. Neef et al. Heterocylces 20, 1295,1299 ( 1983 )].

Therefore the object was to develop a process, that because of its good yields with good handling and without purification problems, makes possible the industrial production of these β-carboline-intermediate stages independent of the type of substituent on the indole.

Surprisingly, it has now been found that in the reaction of indoles with imines in the presence of phosphoric acid the desired intermediate products for the production of pharmacologically valuable β-carbolines result in good up to very good yields.

Another advantage of the process according to the invention consists in the fact that only easily separable and nonpolluting by-products result.

For example, the alkaline wash waters contain easily soluble dipotassium hydrogen phosphate and aldehyde from the excess imine that is oxidized with hydrogen peroxide to the potassium salt of carboxylic acid. Then the phosphate is removed from the wash waters as the slightly soluble calcium hydrogen phosphate-dihydrate.

The invention relates to the process for the production of compounds of formula I

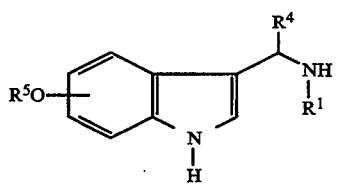

in which
$R^1$ means $C_{1-4}$-alkyl,
$R^4$ means hydrogen, $C_{1-4}$-alkyl or $C_{1-4}$-alkoxy-$C_{1-2}$-alkyl and
$R^5$ means $C_{1-4}$-alkyl or an optionally substituted phenyl or phenyl-$C_{1-2}$-alkyl radical, and $-OR^5$ can be single or multiple characterized in that a compound of formula II

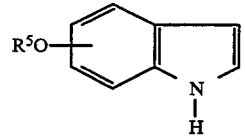

in which $R^5$ that has the above indicated meaning is reacted in the presence of phosphoric acid with an imine of formula III $$R^4-CH{=}N-R^1 \qquad III.$$

in which $R^4$ and $R^1$ have the above meaning.

Substituent $-OR^5$ can be in 4, 5, 6 and/or 7 position singly or multiply, especially single or double, and the single substitution in 4 or 5 position is preferred.

By $C_{1-4}$-alkyl is meant respectively a straight or branched alkyl group, such as methyl, ethyl, propyl, isopropyl, butyl, sec. butyl, tert. butyl and isobutyl.

As phenyl-$C_{1-2}$-alkyl radical $R^5$ there can be mentioned, for example, benzyl, phenethyl and β-methylbenzyl. The phenyl radical and the phenyl-$C_{1-2}$-alkyl radical can be substituted singly or doubly in any position and single substitution is preferred.

As substituents of the phenyl radical there can be mentioned, for example, halogens, $C_{1-4}$-alkyl, $C_{1-4}$-alkoxy, trifluoromethyl, cyano or nitro, and the substitution with halogens is preferred.

As the substituents of the phenyl-$C_{1-2}$-alkyl radical, halogens, $C_{1-4}$-alkyl, $C_{1-4}$-alkoxy, trifluoromethyl or cyano are especially suitable, and halogens are preferred substituents.

Halogen respectively comprises fluorine, chlorine, bromine or iodine.

As a preferred substituent combination, phenyl optionally substituted with halogen and benzyl optionally substituted with halogen are to be considered, $R^4$ means preferably $C_{1-4}$-alkoxy-$C_{1-2}$-alkyl and $R^1$ is especially isopropyl.

The reaction according to the invention is performed in the presence of molar amounts of phosphoric acid or with an excess of phosphoric acid at temperatures of $-20°$ C. to room temperature, preferably at $-10°$ C. to $+10°$ C., and is generally completed after a ½ hour up to 3 hours.

Suitably the phosphoric acid is dissolved in protic or polar solvents such as alcohols or ethers, for example, methanol, ethanol, propanol, i.a., and reacted with equivalent amounts or an excess of imine, optionally dissolved in an inert solvent, and with the corresponding indole. As inert solvent, hydrocarbons, chlorinated hydrocarbons and cyclic or acyclic ethers can be considered. The reaction can also take place in a suspension.

The invention further relates to the new initial compounds of formula IIa

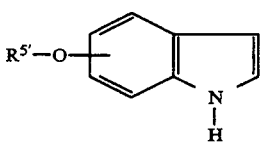

in which R⁵'means an optionally substituted phenyl and —OR⁵'is in 4 or 5 position.

The production of the compounds of formula IIa takes place according to known methods, by a compound of formula IV

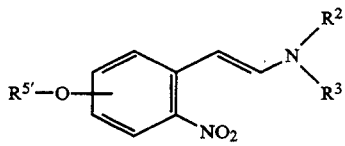

in which R⁵'has the above meaning, for R⁵ and R² and R³ are the same or different, and each mean $C_{1-4}$-alkyl or together with the nitrogen atom a saturated five or six ring radical optionally containing another nitrogen, oxygen or sulfur atom, being catalytically reduced and cyclized.

As saturated five or six ring radicals there can be mentioned, for example: imidazolidine, pyrrolidine, piperidine, morpholine, thiomorpholine, piperazine.

As catalysts for the reduction according to the invention the usually used hydrogenation catalysts are suitable such as, for example, Raney nickel or noble metal catalysts such as platinum oxide or palladium/carbon. The cyclization takes place at room temperature or with heating to 50° C. at hydrogen normal pressure or elevated hydrogen pressure in an aqueous suspension or in inert solvents such as alcohols, esters or ketones or their mixtures. In the course of the reaction according to the invention the $NR^2R^3$ group is cleaved off (W. Leimgruber and A. D. Batcho, Org. Synth. 63, 214 (1985).

The compounds of formula I are further processed to the compounds described in EP-A-54 507, EP-A-239 667, EP-A-234 173 and EP-A-130 140 according to methods described there.

The production of the initial compounds is known or takes place according to methods known or described here.

The following examples are to explain the process according to the invention.

EXAMPLES

Production of the Initial Compounds a) 4-(4-Chlorophenoxy)-indole

6-Amino-2-nitrotoluene in aqueous 48 percent hydrobromic acid is diazotized with sodium nitrite and is converted according to Sandmeyer with copper(I)-bromide into the desired 6-bromo-2-nitro-toluene. Under modified Ullmann conditions (copper(I)-chloride, adding of a solid-liquid phase-transfer catalyst such as TDA-1 [tris-(3,6-dioxaheptyl)-amine]), 6-bromo-2-nitro-toluene is reacted with the potassium salt of 4-chlorophenol in-a high-boiling solvent to the diarylether 6-(4-chlorophenoxy)-2-nitrotoluene (G. Soula, J. Org. Chem.50, 3717 (1985)).

Analogously to the method according to Leimgruber-Batcho without isolation the 6-(4-chlorophenoxy)-2-nitro-β-pyrrolidino styrene is reductively cyclized with Raney nickel/hydrogen from 6-(4-chlorophenoxy)-2-nitrotoluene to 4-(4-chlorophenoxy)-indole.

b) N-isopropyl N-(2-methoxyethylidene)-amine 144 ml of isopropyl amine is dissolved in 225 ml of toluene under nitrogen atmosphere. With ice water cooling and stirring 112.5 ml of methoxyacetaldehyde is instilled within 40 minutes and is allowed to stir for 30 minutes more under cooling. After turning off of the stirrer the reaction volume is cooled with ice water for 30 minutes, the lower phase is pipetted off. After addition in portions of 75 g of potassium carbonate, the toluene solution is stirred for 3 hours more under nitrogen, the potassium carbonate is filtered off and it is washed three times more with 130 ml of toluene each. The solution, filled up with toluene to 800 ml total volume, is stored in the freezer until use.

c) N-isopropyl-N-methylene amine

As described in b), 750 ml of a solution of N-isopropyl-n-methylene amine in toluene is obtained from 144.0 ml of isopropyl amine and 125.2 ml of 37% aqueous formaldehyde solution.

d) N-ethylidene-N-isopropyl amine 48.0 ml of isopropyl amine and 31.6 ml of acetaldehyde is reacted analogously to b). The imine of the acetaldehyde dissolved in 225 ml of toluene is obtained.

e) N-isopropyl-N-propylidene amine 72.0 ml of isopropyl amine and 60.3 ml of propionaldehyde are reacted to 420 ml of a solution of imine in toluene analogously to b).

Example 1

17.86 g of 100% phosphoric acid is dissolved in 32.2 ml of ethanol at room temperature and cooled to −5° C. 9.75 g of 4-(4-chlorophenoxy)-indole, dissolved in 32.4 ml of imine solution, is instilled in the cooled solution of phosphoric acid within 30 minutes at an internal temperature below +10° C. It is allowed to stir for 1 hour more at +10° C. After addition of 35.7 ml of toluene and 71.5 ml of water the phases are thoroughly mixed vigorously for 15 minutes, the separated toluene phase is washed once with 18.0 ml of water. The combined aqueous phases are concentrated by evaporation in a vacuum at +40° C. bath temperature to 25 ml of volume, the residual solution is diluted with 25 ml of water. The cooled reaction mixture is adjusted to pH 9.5 with 50% potassium hydroxide solution, the precipitated precipitate is suctioned off, washed with water and dried in a vacuum at room temperature over KOH up to constant weight. 6.0 g yield (42% of theory) of N-(1-[4-(4-chlorophenoxy)-indol-3-yl]-2-methoxyethyl)-N-isopropylamine of melting point of 149.4°–150° is obtained.

Example 2

Analogously to example 1, 43.2 g (yield 82.7% of theory) of N-[1-(4-benzyloxy-indolyl-3-yl)-2-methoxyethyl]-N-isopropylamine of a melting point of 138.4-139.3° C is obtained from 34.47 g of 4-benzyloxy-indole.

Example 3

By addition of 22.3 g of 5-benzyloxy-indole and imine as suspension as indicated in example 1 to the phosphoric acid solution in ethanol, 24.35 g (72% of theory) of the 5-benzyloxy indole pseudogramine of a melting point of 108.7°–110.3° C. is isolated.

Example 4

By reaction of 6.09 g of 4-(4-chlorophenoxy)-indole with 19.05 ml of imine solution c) as described in example 1, 3.70 g (47.0 of theory) of N-1-(4-[-chlorophenoxy]-indol-3-yl)-methyl-N-isopropylamine of a melting point of 88.2°–90.0° C. is obtained.

Example 5

39.2 g (65.8% of theory) of N-[1-(4-benzyloxy indol-3-yl)-ethyl]-N-isopropylamine of a melting point of 143.0° C. is obtained from 50.0 g of 4-benzyloxy indole and 144.0 ml of imine solution d).

Example 6

By addition of 39.7 g of 5,6-dimethoxy indole and 190.5 ml of imine solution e) as suspension for the phosphoric acid dissolved in ethanol, analogously to example 1, 37.15 g of N-isopropyl-N-[1-(5,6-dimethoxyindol-3-yl)-propyl]-amine (60.0% of theory) of a melting point of 124.0°–126.9° C. is obtained.

We claim:

1. A process for the production of compounds of formula I

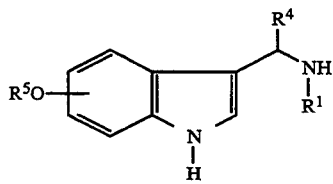

wherein $R^1$ is $C_{1-4}$-alkyl;

$R^4$ is hydrogen, $C_{1-4}$-alkyl or $C_{1-4}$-alkoxy-$C_{1-2}$-alkyl; and $R^5$ is $C_{1-4}$-alkyl, an optionally substituted phenyl or optionally substituted phenyl-$C_2$-alkyl, and $-OR^5$ can be single or multiple, said process comprising reacting a compound of formula II

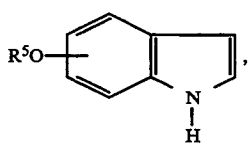

wherein $R^5$ has the meaning indicated above, in the presence of phosphoric acids with a compound of formula III $$R^4-CH=N-R^1 \quad \text{III,}$$

wherein $R^4$ and $R^1$ have the meanings indicated above.

2. A compound of formula IIa

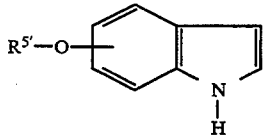

wherein $R^{5'}$ is a phenyl mono- or disubstituted by halogen, $C_{1-4}$-alkyl, $C_{1-4}$-alkoxy, trifluoromethyl, cyano and/or nitro.

3. A process according to claim 1, wherein said compound of formula II contains one or two $OR^5$ groups, wherein $R^5$ is $C_{1-4}$-alkyl, phenyl, phenyl-$C_{1-2}$-alkyl, phenyl monosubstituted or disubstituted by halogen, $C_{1-4}$-alkyl, $C_{1-4}$-alkoxy, trifluoromethyl, cyano and/or nitro, or phenyl-$C_{1-2}$-alkyl monosubstituted or disubstituted by halogen, $C_{1-4}$-alkyl, $C_{1-4}$-alkoxy, trifluoromethyl and/or cyano.

4. A process according to claim 3, wherein said compound of formula II has a $-OR^5$ substituent in the 4- and/or 5-position.

5. A process according to claim 3, wherein $R^5$ is benzyl, phenethyl or β-methylbenzyl.

6. A process according to claim 3, wherein $R^5$ is phenyl; phenyl substituted by fluorine, chlorine, bromine or iodine; benzyl; or benzyl substituted by fluorine, chlorine, bromine or iodine.

7. A process according to claim 6, wherein $R^4$ is $C_{1-4}$-alkoxy-$C_{1-2}$-alkyl.

8. A process according to claim 7, wherein $R^1$ is isopropyl.

9. A process according to claim 3, wherein the reaction of said compound of formula II and said compound of formula III is conducted at a temperature of $-20°$ C. to room temperature.

10. A process according to claim 9, wherein said reaction is conducted at $-10°-+10°$ C.

11. A compound according to claim 2, wherein $OR^{5'}$ is in the 4- or 5-position.

12. A process according to claim 1, wherein $-OR^5$ is 4-chlorophenoxy, 4-benzyloxy, 5-benzyloxy, or methoxy.

13. A process according to claim 1, wherein said compound of formula III is N-isopropyl-N-(2-methoxyethylidene)-amine, N-isopropyl-N-(methylene-amine), N-ethylidene-N-isopropyl-amine, or N-isopropyl-N-propylidene-amine.

* * * * *